United States Patent [19]
Jani et al.

[11] Patent Number: 6,120,498
[45] Date of Patent: Sep. 19, 2000

[54] ASPIRATING HANDPIECES FOR LASER SURGICAL OPERATIONS

[76] Inventors: Mahendra G. Jani, 7050 E. Sunrise Dr. #1202, Tucson, Ariz. 85750; J. Michael Yarborough, 4101 E. Placita Pequena, Tucson, Ariz. 85718; George Marcellino, 3773 Paul Sweet Rd., Santa Clara, Calif. 95065; Robert W. Snyder, 4091 N. Larrea La., Tucson, Ariz. 85750; Donald J. D'Amico, 37 Wanders Dr., Hingham, Mass. 02043

[21] Appl. No.: 09/035,673

[22] Filed: Mar. 5, 1998

[51] Int. Cl.⁷ ................................................. A61B 17/36
[52] U.S. Cl. ............................ 606/16; 606/15; 606/4; 606/6; 604/35
[58] Field of Search .................. 606/2, 2.5, 4, 5, 606/6, 7–10, 13–16, 41, 45, 49; 607/88, 89, 92, 93; 604/19, 20, 35

[56] References Cited

U.S. PATENT DOCUMENTS

| | | |
|---|---|---|
| 4,055,167 | 10/1977 | Bernstein . |
| 4,207,874 | 6/1980 | Choy . |
| 4,538,608 | 9/1985 | L'Esperance, Jr. . |
| 4,627,436 | 12/1986 | Leckrone . |
| 4,672,969 | 6/1987 | Dew . |
| 4,694,828 | 9/1987 | Eichenbaum ........................ 128/303.1 |
| 4,869,246 | 9/1989 | Adair ........................................ 606/7 |
| 4,963,142 | 10/1990 | Loertscher ............................... 606/14 |
| 4,985,027 | 1/1991 | Dressel ..................................... 606/15 |
| 5,241,990 | 9/1993 | Cook . |
| 5,246,436 | 9/1993 | Rowe ....................................... 606/13 |
| 5,254,114 | 10/1993 | Reed, Jr. et al. ........................ 606/15 |
| 5,263,950 | 11/1993 | L'Esperance, Jr. ....................... 606/6 |
| 5,267,996 | 12/1993 | Fletcher .................................. 606/17 |
| 5,285,795 | 2/1994 | Ryan et al. ............................. 128/750 |
| 5,318,560 | 6/1994 | Blount et al. .............................. 606/4 |
| 5,321,715 | 6/1994 | Trost ........................................ 372/69 |
| 5,334,140 | 8/1994 | Phillips .................................... 604/35 |
| 5,335,671 | 8/1994 | Clement ................................. 128/753 |
| 5,358,505 | 10/1994 | Wuchinich ............................... 606/99 |
| 5,364,391 | 11/1994 | Konwitz ................................... 606/16 |
| 5,423,798 | 6/1995 | Crow ......................................... 606/4 |
| 5,507,742 | 4/1996 | Long et al. .............................. 606/15 |
| 5,693,044 | 12/1997 | Cosmescu ............................... 606/42 |
| 5,738,680 | 4/1998 | Mueller et al. ......................... 606/15 |

FOREIGN PATENT DOCUMENTS

| | | |
|---|---|---|
| 0 248 520 | 12/1987 | European Pat. Off. . |
| 0 342 448 | 11/1989 | European Pat. Off. . |
| 37 07 921 | 3/1987 | Germany . |
| 3822011 A1 | 1/1990 | Germany . |
| 42 36 329 | 10/1992 | Germany . |
| WO 89/03202 | 4/1989 | WIPO . |
| WO 91/05332 | 4/1991 | WIPO . |
| WO 91/06271 | 5/1991 | WIPO . |
| WO 93/01756 | 2/1993 | WIPO . |
| WO 93/12728 | 7/1993 | WIPO . |
| WO 96/32895 | 10/1996 | WIPO . |

OTHER PUBLICATIONS

Coherent Booklet, "Treating Prostate Problems," copyright 1991, 1994 by Krames Communications, pp. 1–15.

D. Paulson, "Diseases of the Prostate," *Clinical Symposia*, vol. 41, No. 2, 1989, pp. cover, 1–32.

*Primary Examiner*—Linda C. M. Dvorak
*Assistant Examiner*—Bryan K. Yarnell

[57] ABSTRACT

An aspirating handpiece for laser surgical applications, includes an elongated hollow cylindrical probe member (22). A proximal end (24) of the probe member is arranged such that aspiration means can be connected therewith, and a distal end (26) of the probe member has an aperture therein for receiving matter to be aspirated. An elongated optical fiber (50) extends along the probe member with the distal end (59) of the fiber proximate the aperture therein. The proximal end (52) of the fiber is arranged to receive laser radiation. The probe member has an inside diameter progressively increasing from the distal end thereof to the proximal end thereof.

9 Claims, 2 Drawing Sheets

ASPIRATING HANDPIECES FOR LASER SURGICAL OPERATIONS

TECHNICAL FIELD OF THE INVENTION

The present invention relates generally to handpieces for delivering laser radiation to tissue to be irradiated in laser surgical operations. It relates in particular to handpieces including an optical fiber for delivering the radiation and an aspirating arrangement for removing debris resulting from the laser irradiation.

DISCUSSION OF BACKGROUND ART

For precision laser surgical operations such as cataract surgery, the surgical instrument of choice is a handpiece including an optical fiber along which laser radiation is delivered to a site being treated and a vacuum aspiration arrangement for removing any debris resulting from the treatment. One particular example is a laser handpiece used for ophthalmic laser surgery operations such as cataract removal. In such a handpieces, aspiration of debris takes place via a tube or conduit while delivery of laser radiation is delivered by a fiber which extends along or through the tube with the tip of the fiber located proximate a distal aperture of the tube.

For reasons of precision, the aspiration tube must be relatively small in diameter. For example small enough to fit within the lens capsule of an eye for extracting therefrom debris remaining after a foreign body located in the lens capsule has been shattered or ablated by laser radiation in a lensectomy. In prior art handpieces, this relatively small diameter frequently results in clogging of the tube, with consequent interruption of an operation while the clogging is cleared or a clogged handpiece is replaced.

A further problem with prior-art aspirating handpieces is that they are often unsuitable, by virtue of the dimensions of the aspiration arrangement, for phases of an operation in which a higher precision or precise penetration is required without the need for simultaneous aspiration. Typically in such an operation a non-aspiration handpiece may be used to fragment a foreign object in a bodily cavity, and an aspirating handpiece used to ablate fragments of the foreign object and aspirate the ablation products from the cavity. This of course requires changing a handpiece during an operation.

Changing handpieces may be required many times during an operation thus adding significantly to the duration of the operation. This, combined with the cost of the additional handpieces adds to the cost of the operation. Further, constant insertion and removal of the different handpieces through an incision in the eye can cause excessive manipulation of sensitive intraocular tissue, potentially resulting in over hydration of the cornea.

SUMMARY OF THE INVENTION

In one aspect of the present invention, a handpiece for delivering laser radiation to a site for treating biological material at the site and for aspirating treated material from the site comprises an elongated hollow cylindrical probe member having proximal and distal ends. The proximal end of the probe member is arranged such that aspiration means can be connected therewith. The distal end of said probe member has an aperture therein for receiving treated biological material to be aspirated. An elongated optical fiber having a proximal and a distal end is arranged to receive the laser radiation at the proximal end thereof for delivery to the material to be treated thereby. The elongated fiber extends along the probe member with the distal end of the fiber being proximate the aperture in the probe member. The clogging problem is addressed in that the probe member has an inside diameter progressively increasing from the distal end thereof to the proximal end thereof.

In a preferred embodiment of the present invention the hollow cylindrical member is open at the distal end thereof such that the treated-matter receiving aperture is located on the cylindrical axis thereof, thereby permitting treated matter to aspirated axially or longitudinally into the probe member. The elongated fiber extends through the hollow probe member and is arranged such that the location of the distal end of the fiber with respect to the treated-matter receiving aperture is variable. This permits the fiber to be extended through the treated-matter receiving aperture to a first position beyond the aperture for treating material without aspiration, and retracted to a second position closer to the aperture than the first position for treating and aspirating material.

Preferably the fiber is arranged such that it extends through the hollow probe member with the fiber axis laterally displaced from the cylindrical axis of the probe member and with the fiber located in a longitudinal groove in the wall of the probe member at the distal end thereof. This minimizes obscuration of the treated-matter receiving aperture therein and minimizes resistance to the aspiration of treated matter through the probe member.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Figure 1:
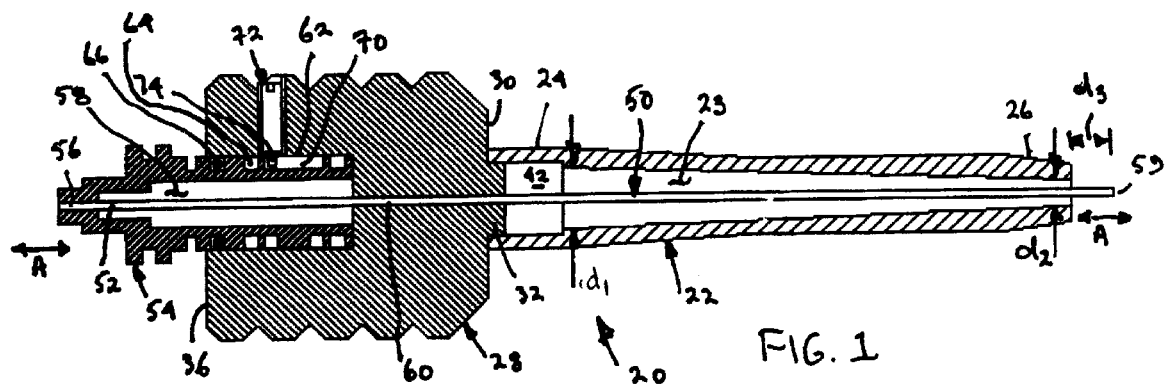
FIG. 1 is a cross-section view schematically illustrating one preferred embodiment of a handpiece in accordance with the present invention including a hollow cylindrical probe member having an optical fiber extending axially therethrough and extending therefrom though a treated matter receiving aperture therein at a distal end thereof, the optical fiber having a connector arrangement attached thereto at a proximal end thereof for coupling with a source of laser radiation.
Figure 2:
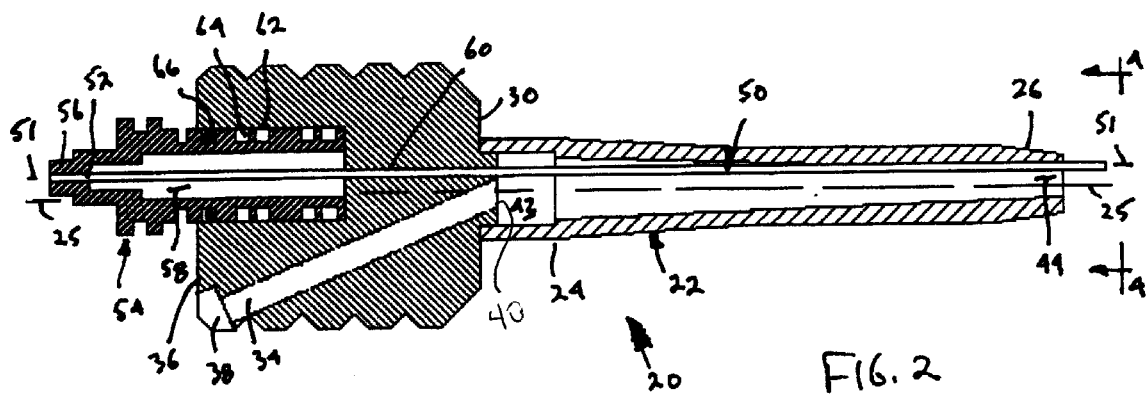
FIG. 2 is a cross section view seen generally in a direction 2—2 of FIG. 1 schematically illustrating displacement of the fiber with respect to the cylindrical axis of the hollow probe member, and an arrangement for connecting a proximal end of the probe member with a vacuum pump or the like for providing aspiration.
Figure 3:
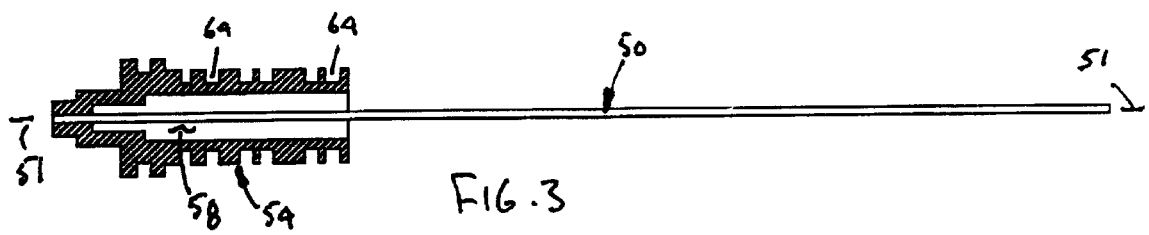
FIG. 3 is a cross section view separately illustrating the optical fiber and connecting arrangement of FIG. 2.

Turning now to the drawings, wherein like features are designated by like reference numerals, FIG. 1 and FIG. 2 schematically illustrate one preferred embodiment 20 of a handpiece in accordance with the present invention. Handpiece 20 includes probe member 22 having a proximal end 24 and a distal end 26. Probe member 22 is open at both the proximal and distal ends thereof. Open proximal end 24 of the probe member is attached, for example by epoxy bonding or silver soldering, to a handpiece body 28 at a front end 30 thereof via a boss 32 thereon. A conduit 34 (see FIG. 2) extends through handpiece body 28 from a rear end 36 thereof to front end 30 thereof. Provision is made at a rear end 38 of conduit 34 for attaching the conduit to a vacuum pump or the like (not shown) for providing an aspiration force or suction. Conduit 34 is in fluid communication, via a front end 40 thereof, with probe member 22 via chamber 42 thereof. Open distal end 26 of probe member 22 provides an aperture 44 in the probe member through which material to be aspirated can be drawn into the probe member.

An elongated optical fiber 50 is provided for delivering laser radiation to material to be treated and subsequently or simultaneously aspirated. A proximal end 52 of the optical fiber is attached to an elongated cylindrical connector unit 54. The fiber is coaxially aligned in the connector unit via a close fitting aperture 56 therein. Preferably the fiber is "potted" into the connector unit by filling space 58 therein with an epoxy or the like.

The assembly of optical fiber 50 and connector unit 54 is assembled into handpiece 20 by passing fiber 50 through a narrow, close-fitting bore 60 in handpiece body 28 extending completely through the handpiece body and inserting connector unit 54 into a wider close-fitting socket 62 in the handpiece body.

Connector unit 54 is provided with circumferential grooves 64 each for accommodating an "O-ring" type seal 66. The seal prevents air leakage between connector 54 unit and the probe member. Any such leakage may reduce the aspiration effectiveness of the handpiece. Seal 66 also allows connector unit 54 to be moved longitudinally in socket 62, which is advantageous for reasons discussed herein below.

Probe member 22 is arranged such that the inside diameter $d_1$ at proximal end 24 thereof is greater than the inside diameter $d_2$ at the distal end thereof. Preferably $d_1$ is greater than 1.5 times $d_2$ and is most preferably about two or more times greater that $d_2$. For a probe member 22 of length about 1.12 inches, a diameter $d_2$ of about 0.05 inches and a diameter $d_1$ of about 0.10 inches provides a frustro-conical hollow interior or canula 23 in probe member 22 with a cone half-angle of about 1°.

The frustro-conical arrangement of canula 23 in probe member 22 is effective in preventing clogging as fragments must be smaller than the distal-end aperture 44 in order to be aspirated. This eliminates clogging of the wider proximal portion of the canula.

Prevention of clogging prevents surges of intraocular pressure (IOP) which would otherwise result as the aspiration system reacted to clogging and subsequent return of flow. Surges in IOP can be serious, as a sudden reduction in IOP can cause collapse of the anterior chamber of the eye, endangering viability of corneal endothelial cells.

Figure 4:
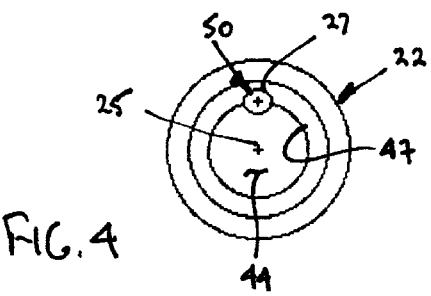
FIG. 4 is an end elevation view seen generally in a direction 4—4 of FIG. 2. schematically illustrating the fiber located in a groove in the wall of the cylindrical probe member and extending through the treated matter receiving aperture therein at the distal end thereof.

Bore 60 and socket 62 are arranged such that the common longitudinal axis 51 of fiber 50, connector unit 54 and apertures 60 and 62 is laterally displaced with respect with respect to longitudinal axis 25 of probe member 22 (see FIG. 2). The displacement is selected such that fiber 50 at distal end 26 of probe member 22 is located in a longitudinal groove 27 in an inner wall 47 of probe member 22 as illustrated in FIG. 4. Groove 27 provides lateral support and constraint for fiber 50 and also provides that fiber 50 does not cause any significant obscuration of aperture 44. Preferably common longitudinal axis 51 is inclined at a small angle with respect to longitudinal axis 25 of probe member 22, for example about by about 1°, such that axis 51 and axis 25 diverge toward distal end 26 of probe member 22. A resulting flexure of fiber 50 provides a force or pressure for retaining the fiber in groove 27.

Handpiece 20 incorporates an arrangement for providing that fiber 50 may be selectively extended beyond aperture 44 of probe unit 22. In one preferred arrangement, a longitudinal slot 70 is provided in connector unit 54 (see FIG. 1). A set-screw 72 extends through handpiece body 28 with the tip 74 thereof in slot 70. Tip 74 of set-screw 72 provides a positive stop for limiting axial motion of connector unit 54 in socket 62. The axial position of connector unit 54 determines a distance $d_3$ by which distal end 59 of fiber 50 protrudes beyond aperture 44. Distance is adjusted by sliding the connector unit in socket 62 as indicated in FIG. 1 by arrows A. Screw 72 may be tightened to clamp connector unit 54 in a selected axial position.

By way of example, the arrangement of set screw 72 and slot 70 provides, in an ophthalmic surgical operation such as a lensectomy, that distal end or tip 59 of fiber 50 can be extended by about 0.25 inches for penetrating a lens capsule and delivering radiation to a foreign body therein thereby breaking up the foreign body into pieces. Fiber 50 may then be retracted by partially withdrawing connector unit 54 from socket 62 such that distal end 59 of fiber 50 is about flush with aperture 44 in probe unit 22. Radiation may then be delivered to pieces of the foreign body to ablate them, while aspiration by probe member 22 draws the ablated material out of the lens cavity into aperture 44, and eventually out of the handpiece via conduit 34.

Figure 5:
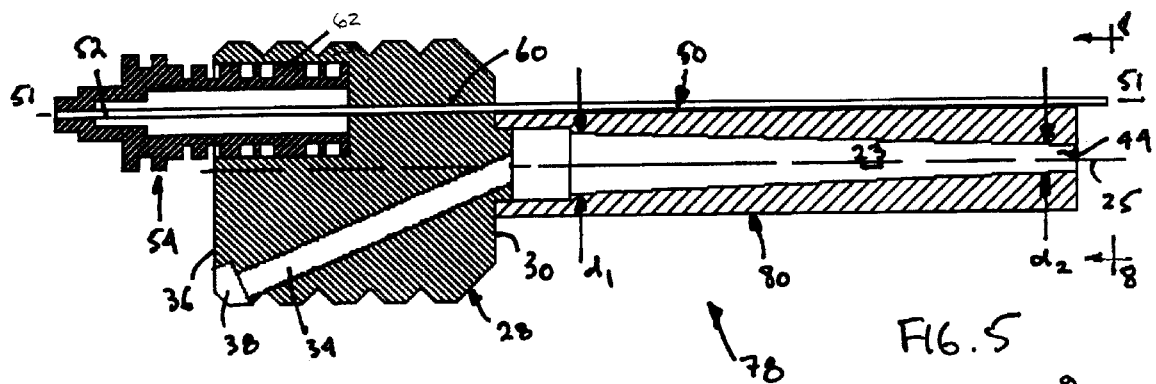
FIG. 5 is a cross-section view schematically illustrating another preferred embodiment of a handpiece in accordance with the present invention including a hollow cylindrical probe member having an optical fiber extending axially therealong on the outside thereof, with the distal end of the optical fiber proximate an axially located aperture in the distal end of the probe member, and wherein the probe member has a constant outside diameter and a inside diameter progressively increasing from the distal end thereof to the proximal end thereof.

Referring now to FIG. 5, another embodiment 78 of an aspirating handpiece in accordance with the present invention is illustrated. Handpiece 78 is similar in most respects to above-described handpiece 20 with the exception that it includes a straight-sided, hollow cylindrical probe member 80, and bore 60 and socket 62 in handpiece body 28 are located such that fiber 50 extends along probe member 80 on the outside thereof. Probe member 80 is attached at proximal end 82 thereof to handpiece body 28 and has an axially located aperture 86 at distal end 84 thereof. In accordance with principles of the present invention, inside diameter $d_1$, of probe member 80 at the proximal end 82 thereof is greater than inside diameter $d_2$ at distal end 84 thereof, as specified above for probe member 22.

Connector unit 54 is slidably located in socket 62 of handpiece body 28 to allow the distance between the distal end 59 of fiber 50 and aperture 86 to be varied for reasons exemplified above.

Figure 6:
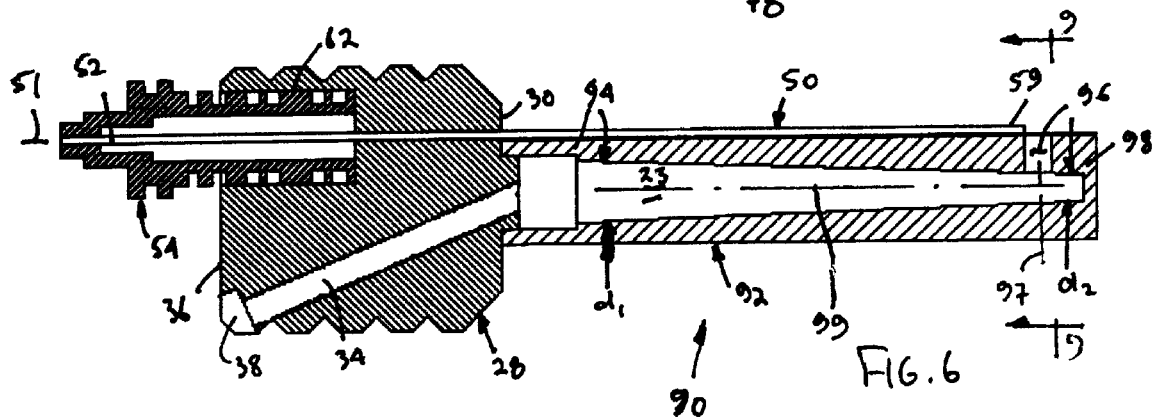
FIG. 6 is a cross-section view schematically illustrating yet another preferred embodiment of a handpiece in accordance with the present invention including a hollow cylindrical probe member closed at the distal end thereof and having an optical fiber extending axially therealong on the outside thereof, with the distal end of the optical fiber located proximate an aperture in the wall of the probe member, and wherein the probe member has a constant outside diameter and an inside diameter progressively increasing from the distal end thereof to the proximal end thereof.

Referring now to FIG. 6, yet another embodiment 90 of a handpiece in accordance with the present invention is illustrated. Handpiece 90 is similar in most respects to above-described handpiece 78 with the exception that it includes a straight-sided, hollow cylindrical probe member 92, attached at proximal 94 thereof to handpiece body 28. Distal end 98 of probe member 92 is axially closed. An aperture 96 extends laterally (transversely) through wall 93 of probe member 92 proximate distal end 98 thereof, into the hollow interior thereof for admitting matter to be aspirated. Aperture 96 has its longitudinal axis 97 about perpendicular to cylindrical axis 99 of probe member 92. In accordance with principles of the present invention, inside diameter $d_1$, of probe member 92 at the proximal end 94 thereof is greater than inside diameter $d_2$ at distal end 98 thereof, as specified above for probe member 22.

Connector unit 54 is preferably fixedly located in socket 62 of handpiece body 28 to such that distal end (tip) 59 of fiber 50 is immediately adjacent aperture 96. This arrangement of fiber and aperture permits material to be ablated having a larger dimension than the aperture to be drawn toward the aperture and held by an aspiration force applied to probe member 96. The material is then ablated, liquified or fragmented by radiation delivered thereto via fiber 50. The aspiration force draws the ablated, liquified or fragmented material into and along the probe member.

One such application in ophthalmic surgery is a vitrectomy, wherein the vitreous humor, a loosely formed gel, is cut or fragmented and removed by aspiration. With conventional vitrectomy instruments, aspiration can cause traction on the retina with the potential of causing a tractional retinal detachment. A handpiece in accordance with the present invention prevents retinal traction by disrupting the structural organization of (liquefying) the vitreous humor with laser energy. Aspiration removes the liquified product without causing retinal traction.

Figure 7:
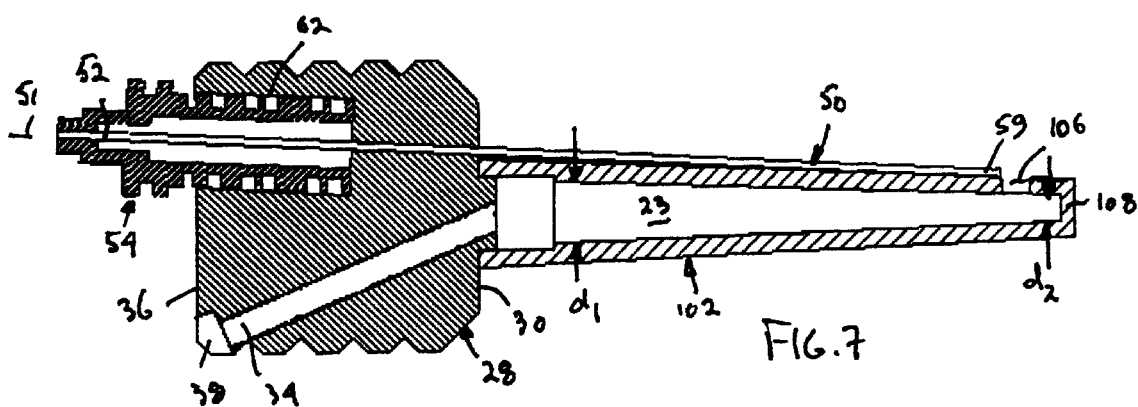
FIG. 7 is a cross-section view schematically illustrating still another preferred embodiment of a handpiece in accordance with the present invention, including a hollow tapered cylindrical probe member closed at the distal end thereof and having an optical fiber extending axially therealong on the outside thereof, with the distal end of the optical fiber located proximate an aperture in the wall of the probe member, and wherein the probe member has an essentially constant wall thickness and the inside diameter of the probe member progressively increases from the distal end thereof to the proximal end thereof.

Referring now to FIG. 7, still another embodiment 100 of an aspirating handpiece in accordance with the present invention is illustrated. Handpiece 100 is similar in most respects to abovedescribed handpiece 90 with the exception that it includes a tapered, hollow cylindrical probe member 102, attached at proximal end 104 thereof to handpiece body 28. Distal end 108 of probe member 92 is axially closed. Probe member 102 tapers from a widest outside diameter at proximal end 104 thereof to a narrowest outside diameter at distal end 108 thereof. An aperture 106 extends laterally through wall 103 of probe member 102 proximate distal end 108 thereof, in the manner described above for aperture 96 of probe member 93. In accordance with principles of the present invention, inside diameter $d_1$, of probe member 92 at the proximal end 94 thereof is greater than inside diameter $d_2$ at distal end 98 thereof, as specified above for probe member 22. The outside diameter of probe member 102 may be tapered in the manner of the inside diameter such that wall 103 of the probe member has a constant thickness. This arrangement provides a relatively short length of aperture 106 which reduces the possibility of clogging the aperture. Handpiece 100 operates in the manner of handpiece 90 and is suitable for like operations.

Figure 9:
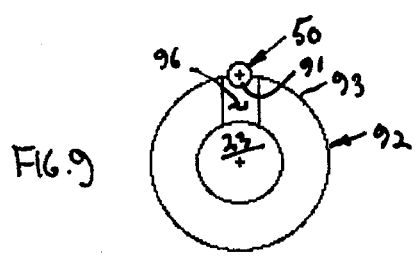
FIG. 9 is a end elevation view seen generally in the direction 9—9 of FIG. 6, schematically illustrating the fiber retained in a groove in an outer wall of the distal end of the probe member.
Figure 8:
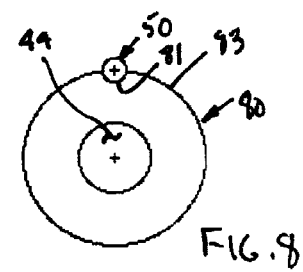
FIG. 8 is a end elevation view seen generally in the direction 8—8 of FIG. 5, schematically illustrating the fiber retained in a groove in an outer wall of the distal end of the probe member.

In all of the handpieces 78, 90 and 100, it is preferable that fiber 50 be retained in a longitudinal groove, at least at the distal end of probe the probe member. This is illustrated in FIG. 8 for probe member 80 of handpiece 78, wherein fiber 50 is located in a longitudinal groove 81 in an outer wall 83 of probe member 80. Groove 81 prevents lateral movement of fiber 50 with respect to probe member 80. Axis 51 of connector unit 54 is preferably tilted by a small angle, for example by about 1°, such that axes 51 and 25 converge toward the distal end of the probe member providing pressure for retaining the fiber in the groove. A similar arrangement is illustrated in FIG. 9 for probe member 92 of handpiece 90, wherein fiber 50 is located in a longitudinal groove 91 in an outer wall 93 of probe member 92.

It should be noted here that while operation of handpieces in accordance with the present invention has been described with reference to ophthalmic surgical operations, use of the handpieces is not limited to such operations. The inventive handpieces are useful in operations such as laser-assisted removal of damaged cartilage; tympanoplasty; intraventricular neurosurgery; dissection of spinal cord neoplasms, and intracardial, ablation, excision or fistulization. The inventive handpieces are also useful for laser-assisted procedures in arthroscopic operations.

It should also be noted that use of the inventive handpieces is not limited to delivery of laser radiation of any particular wavelength. The inventive handpieces are suitable for delivering laser radiation of any wavelength for which transmissive fibers are available.

The present invention has been described and depicted in terms of a preferred and other embodiments. The invention is not limited, however, to those embodiments described and depicted. Rather the invention is defined by the claims appended hereto.

What is claimed is:

1. A handpiece for laser surgical applications, the handpiece for delivering laser radiation from a laser to a site for treating biological material at the sites, and connectable with a vacuum pump for aspirating treated material from the site, comprising:

an elongated hollow cylindrical probe member having proximal and distal ends, having an inside diameter progressively increasing from the distal end thereof to the proximal end thereof, and having a groove in an inner wall thereof at the distal end thereof; the proximal end of said probe member arranged such that the vacuum pump can be connected therewith for providing an aspiration force within said probe member and the distal end of said probe member having an aspiration aperture axially located therein at the distal end thereof for receiving treated material to be aspirated; and an elongated optical fiber having a proximal and a distal end, the proximal end of said fiber arranged to receive laser radiation from the laser for delivery to the material to be treated, said elongated fiber extending along said probe member on the inside thereof, with the longitudinal axis of said optical fiber laterally displaced from the cylindrical axis of said probe member and with the optical fiber located in said groove at the distal end of said probe member with the distal end of said fiber proximate said aspiration aperture therein.

2. The handpiece of claim 1, wherein said optical fiber is movable with respect to said probe member for selectively positioning the distal end of said fiber relative to the distal end of said probe member.

3. A handpiece for laser surgical applications, the handpiece for delivering laser radiation from a laser to a site for treating biological material at the sites and connectable to a vacuum pump for aspirating treated material from the site, comprising:

an elongated hollow cylindrical probe member having proximal and distal ends and having an inside diameter progressively increasing from the distal end thereof to the proximal end thereof, the proximal end of said probe member arranged such that the vacuum pump can be connected therewith for providing an aspiration force within said probe member and the distal end of said probe member having an axially located aspiration aperture therein for receiving treated material to be aspirated;

an elongated optical fiber having a proximal and a distal end, the proximal end of said fiber arranged to receive laser radiation from the laser for delivery to the material to be treated and said elongated fiber extending along said probe member on the inside thereof, with the longitudinal axis of said optical fiber laterally displaced from the cylindrical axis of said probe member, said optical fiber being located in a groove in an inner wall of said probe member at the distal end thereof; and wherein said optical fiber is movable with respect to said probe member for selectively positioning the distal end of said fiber relative to said aperture in said probe member.

4. The handpiece of claim 3, wherein said probe member is attached to a cylindrical handpiece body at a first end thereof; said optical fiber is mounted at the proximal end thereof in a cylindrical connector unit, said connector unit for connecting the fiber to a source of laser radiation, and being slidably located in a socket extending partially into said handpiece body from a second end thereof with said optical fiber extending through a bore extending from said socket through handpiece body at a point on said first end thereof within said probe member; and conduit extends through said body from said second end thereof to a point on said first end thereof within said probe member, said conduit for connecting said probe member with said aspiration means.

5. The handpiece of claim 4 wherein a slidable gas tight seal is provided between said connecting unit and said socket.

6. The handpiece of claim 4 wherein said connector unit is coaxial with said optical fiber and said socket is arranged such that the longitudinal axis of said optical fiber diverges by a relatively small angle from the longitudinal axis of said probe member toward the distal end thereof, thereby creating pressure between said optical fiber and said groove in said inner wall of said probe member for retaining said optical fiber therein.

7. A handpiece for laser surgical applications, the handpiece for delivering laser radiation from a laser to a site for treating biological material at the sites and connectable to a vacuum pump for aspirating treated material from the site, comprising:

an elongated hollow cylindrical probe member having proximal and distal ends, the proximal end of said probe member arranged such that the vacuum pump can be connected therewith for providing an aspiration force within said probe member, the distal end of said probe member having an aspiration aperture therein, axially located at the distal end thereof for receiving treated material to be aspirated, and the distal end of said probe member having a groove in an inner wall thereof; and an elongated optical fiber having a proximal and a distal end, the proximal end of said fiber arranged to receive laser radiation from the laser for delivery to the material to be treated and said elongated fiber extending along said probe member on the inside thereof with the distal end of said fiber proximate said aspiration aperture therein and located in said groove in said inner wall thereof, and wherein said optical fiber is movable with respect to said probe-member for selectively positioning the distal end of said fiber relative to said aperture in said probe member.

8. The handpiece of claim 7 wherein said probe member has an inside diameter progressively increasing from the distal end thereof to the proximal end thereof.

9. A handpiece for laser surgical applications, the handpiece for delivering laser radiation from a laser to a site for treating biological material at the site, and connectable with a vacuum pump for aspirating treated material from the site, comprising:

an elongated hollow cylindrical probe member having proximal and distal ends and having a groove in an inner wall thereof at the distal end thereof, the proximal end of said probe member arranged such that the vacuum pump can be connected therewith for providing an aspiration force within said probe member and the distal end of said probe member having an aspiration aperture axially located therein at the distal end thereof for receiving treated material to be aspirated; and an elongated optical fiber having a proximal and a distal end, the proximal end of said fiber arranged to receive laser radiation from the laser for delivery to the material to be treated, said elongated fiber extending along said probe member on the inside thereof and located in said groove at the distal end of said probe member with the distal end of said fiber proximate said aspiration aperture.

* * * * *